United States Patent [19]

West

[11] Patent Number: 5,224,955
[45] Date of Patent: Jul. 6, 1993

[54] SURGICAL NEEDLE-SUTURE COMBINATION AND APPARATUS AND METHOD FOR ATTACHING THE SAME

[75] Inventor: John L. West, Wolcott, Conn.

[73] Assignee: American Cyanamid Company, Stamford, Conn.

[21] Appl. No.: 746,023

[22] Filed: Aug. 15, 1991

[51] Int. Cl.⁵ .................................. A61B 17/00
[52] U.S. Cl. .................... 606/226; 606/224; 606/225; 163/1
[58] Field of Search .............. 606/222–227; 163/1, 5

[56] References Cited

U.S. PATENT DOCUMENTS

| | | | |
|---|---|---|---|
| 2,411,079 | 11/1946 | Baule | 606/226 |
| 2,620,028 | 12/1952 | Kohut | 606/226 |
| 3,534,740 | 10/1970 | Thompson | 606/226 |
| 3,611,551 | 10/1971 | Shave et al. | 606/226 |
| 3,890,975 | 6/1975 | McGregor | 606/227 |
| 3,910,282 | 10/1975 | Messer et al. | 606/226 |
| 3,924,630 | 12/1975 | Walldorf | 606/226 |
| 4,072,041 | 2/1978 | Hoffman et al. | 606/226 |
| 4,124,027 | 7/1978 | Boss | 606/227 |

FOREIGN PATENT DOCUMENTS

| | | | |
|---|---|---|---|
| 1022734 | 12/1977 | Canada | 26/83 |
| 2459696 | 7/1975 | Fed. Rep. of Germany | 606/226 |

Primary Examiner—Stephen C. Pellegrino
Assistant Examiner—Gary Jackson
Attorney, Agent, or Firm—Charles F. Costello, Jr.

[57] ABSTRACT

An improved surgical needle is disclosed. The needle has a butt. The butt has a proximal and a distal end. A blind hole is in the butt. The hole originates at the proximal and terminates at the distal end of the butt. A crimp is adjacent to the butt. The improvement to the crimp comprises a first and a second side that are essentially parallel. A third side is essentially perpendicular to the first and second sides. A fourth side is curvilinear. The curvilinear fourth side can be a semicircle. A machine and a method of attaching a surgical suture to the improved needle is also disclosed.

5 Claims, 2 Drawing Sheets

SURGICAL NEEDLE-SUTURE COMBINATION AND APPARATUS AND METHOD FOR ATTACHING THE SAME

This is a related application to U.S. Ser. Nos. 07/632,553 filed Dec. 24, 1990 and 07/746,022 filed Aug. 15, 1991.

BACKGROUND OF THE INVENTION

The most common type of surgical needle is a single use needle which is crimped to the end of a suture. The needle is used once and then discarded. It is preferable that the needle have a diameter that is only slightly larger than the suture.

The single use needle can be a "drilled end" needle. In this type of needle a concentric hole is formed, usually by drilling in the butt of the needle. The suture is placed in the hole. The needle is then crimped around the suture. The crimp must be strong enough to enable the suture to remain attached to the needle during the in-vivo placement of the needle and the passing of the suture through tissue.

After the suture approximates the tissue, it is frequently convenient to detach the needle so that the ends of the suture can be tied together without the needle(s). Cutting of the suture with scissors or a scapel is a convenient method of disengaging the needle. This requires an extra instrument and an extra manipulation. Some surgeons use commercially available pull-off needles. The pull-off values for these needles are in conformity with U.S. Pharmacopeia (abbreviated "USP" herein) requirements.

In addition to size of the needle and suture, which can effect the strength of the needle-suture attachment, other variables can be the surface smoothness of the suture and needle lubricants. Some needles are lubricated with a silicone rubber or polytetrafluoroethylene to reduce tissue drag in use. The needle hole can be filled with zylene or another volatile solvent during coating to reduce the penetration of the lubricant into the needle hole.

In many instances each needle-suture combination is nondestructively tested to a minimum pull-off value in routine production. Only those that pass a test load are accepted for further processing.

Conventional crimp operations are difficult to control. Usually, crimping is between dies that close to a fixed gap, and any variation in the crimp dies, the needle size, the hole size and the suture size changes the degree of crimp. Quality control is likewise difficult.

Other approaches such as crimping to a controlled pressure, or using a combined pressure and gap cycle have been considered. The usual approach is to increase the degree of crimp until the crimping shears off the suture on a test sample, then back off on the degree of crimp until the sutures are not sheared off, and pull-off above USP limits, and after testing a representative group of sutures, proceeding to production.

The attachment of surgical needles to surgical sutures is an ongoing mechanical problem which is most challenging. There is a continuous trend towards eyeless needles in which the end of the suture is fixed to the needle so that the suture is pulled axially through the tissue causing a minimum of trauma. The attachment must be one which (a) is predictably secure, (b) causes a minimum of damage to tissue, (c) is convenient for the using surgeon, (d) permits sterilization and (e) entails reasonable costs, so that the suture needle may be attached economically. The attachment must stand up under the rigors of manufacture, sterilization, storage, shipment and use.

In theory, if all process parameters are perfectly controlled, replicate results are obtained. In practice, so many factors enter that adequate control in production is easier to describe than accomplish.

To develop the background of this invention, the following references are disclosed:

U.S. Pat. No. 3,125,095 issued to D. Kaufman, G. Buccino and A. Glick on Mar. 17, 1964 and is entitled "Flexible Stainless Steel Sutures". This patent discloses generally the manufacture of a coated multifilament steel suture, and specifically in FIG. 3 and column 5, lines 19 to 30 the crimping of the same into a drilled end needle.

U.S. Pat. No. 4,054,144 issued to J. Hoffman and P. Marsland on Oct. 18, 1977 and is entitled "Short-Crimp Surgical Needle". Related U.S. Pat. Nos. 4,060,885 and 4,072,041 issued on Dec. 6, 1977 and Feb. 7, 1978, respectively. These patents respectively disclose a needle-suture combination, and a process and dies for manufacturing the same. These patents generally relate to the attaching of a surgical suture to a drilled end needle. There is also a thorough discussion with cited references relating to the background and development of the art.

All of the above cited U.S. patents are incorporated herein by reference.

SUMMARY OF THE INVENTION

The following embodiments summarize the inventions described in this application:

1. A surgical needle having a butt, the butt comprising a proximal and a distal end, and having essentially a circular cross section adjacent to the distal end;

a blind hole in the butt, the hole originating at the proximal end and terminating at about the distal end of said butt; and a crimp adjacent to said butt, the improvement to the crimp comprising a first and a second side that are essentially parallel, the exterior distance between the first and second sides being from about 1 ½ to 3 percent larger than the exterior diameter of said butt adjacent to said distal end, a third side that is essentially perpendicular to the first and second side, and a fourth side that is curvilinear.

2. The needle of embodiment 1 wherein the fourth side describes an arc of a circle.

3. The needle of embodiment 2 wherein the fourth side describes a semicircle.

4. The needle of embodiment 1 wherein the fourth side describes an arc selected from the group consisting of an ellipse, a hyperbola and a parabola.

5. The needle of embodiment 1 to 4 wherein the length of the curvilinear fourth side is at least about 1.1 times greater than the length of the third side.

6. The needle of embodiment 1 or 4 wherein the length of the curvilinear fourth side is at least about 1.7 times greater than the length of the third side.

7. A surgical needle having a butt, the butt comprising a proximal and a distal end, and having essentially a circular cross section adjacent to the distal end;

a blind hole in the butt, the hole originating at the proximal end and terminating at about the distal end of said butt; and a crimp adjacent to said butt, the improvement to the crimp comprising a first and a second side that are essentially parallel, the exterior distance between the first and second sides being from about 1 ½ to 3 percent larger than the exterior diameter of said butt adjacent to said distal end, a third side that is essentially perpendicular to the first and second side, and a convex fourth side, the exterior distance between the third and fourth sides being, on the axial centerline, from about 65 to 85 percent of the exterior diameter of said butt adjacent to said distal end.

8. The needle of embodiment 7 where the fourth side describes a semicircle.

9. A surgical needle-suture combination comprising:
a needle having a butt, the butt comprising a proximal and a distal end, and having essentially a circular cross section adjacent to the distal end;
a blind hole in the butt, the hole originating at the proximal end and terminating at about the distal end of said butt;
a suture strand having two ends, at least one end of the strand inserted into the blind hole; and
a crimp adjacent to said butt, the improvement to the surgical needle-suture combination comprising the crimp having a first and a second side that are essentially parallel, a third side that is essentially perpendicular to the first and second side, and a fourth side that is curvilinear, the length of the curvilinear fourth side being at least about 1.1 times greater than the length of the third side, the exterior distance between the third and fourth sides being, on the axial centerline, from about 65 to 85 percent of the exterior diameter of said butt adjacent to said distal end.

10. The needle-suture combination of embodiment 9 wherein the fourth side is convex.

11. The needle-suture combination of embodiment 10 wherein the fourth side describes a semicircle.

12. The needle suture combination of embodiment 9 or 10 or 11 wherein one end of the suture strand is inserted into the blind hole.

13. The needle-suture combination of embodiment 12 wherein said suture strand is a monofilament.

14. The needle-suture combination of embodiment 13 wherein the exterior distance between the third and fourth sides is from about 70 to 80 percent of the exterior diameter of said butt adjacent to said distal end.

15. The needle-suture combination of embodiment 13 wherein the distance between the proximal end of said butt and the crimp is from about 0.002 to 0.010 inches.

16. The needle-suture combination of embodiment 12 wherein said suture strand is a braid.

17. The needle suture combination of embodiment 16 wherein the exterior distance between the third and fourth sides is from about 65 to 75 percent of the exterior diameter of said butt adjacent to said distal end.

18. The needle-suture combination of embodiment 9 or 10 or 11 wherein the two ends of the suture strand are inserted into the blind hole.

19. The needle-suture combination of embodiment 18 wherein said suture strand is a monofilament.

20. The needle-suture combination of embodiment 19 wherein the exterior distance between the third and fourth sides is from about 65 to 70 percent of the exterior diameter of said butt adjacent to said distal end.

21. A method of manufacturing a surgical needle-suture combination, the surgical needle having a butt, the butt comprising a proximal and a distal end, and having essentially a circular cross section adjacent to the distal end, and a blind hole in the butt, the hole originating at the proximal end and terminating at about the distal end of said butt, and the suture having at least one filament, the method comprising:
placing said butt of said needle between a first and second die, the first die having a first and a second side that are essentially parallel, the distance between the first and second sides being from about 1 ½ to 3 percent larger than the exterior diameter of said butt adjacent to said distal end, a third side that is curvilinear, and an opening, the opening being formed by the edges of the third side being in contact with the opposite edges of the first and second side, the distance between the third side and the opening formed by the first and second sides being, on the axial centerline, from about 65 to 85 percent of the exterior diameter of said butt adjacent to said distal end, and the second die having a planar surface, the planar surface being essentially perpendicular to said first and second side and opposite to the third side of said first die, and the area of said planar surface being larger than the area of said opening of said first die;
moving a threading block adjacent to said proximal end of said butt, the threading block having a slot;
aligning the slot of the threading block with said proximal end of said butt;
inserting at least one end of the suture into said threading block, through said slot and into the blind hole of said needle; and
crimping said butt of said needle onto the at least one end of said suture by closing said first and second die.

22. The method of embodiment 21 after the crimping step comprising individually testing the needle-suture combination to obtain a minimum pull-out value.

23. The method of embodiment 21 or 22 wherein one end of the suture strand is inserted into the blind hole.

24. The method of embodiment 23 wherein said suture strand is a monofilament.

25. The method of embodiment 24 wherein the distance between the third side and the opening is from about 70 to 80 percent of the exterior diameter of said butt adjacent to said distal end.

26. The method of embodiment 24 wherein the distance between the proximal end of said butt and the crimp is from about 0.002 to 0.010 inches.

27. The method of embodiment 23 wherein said suture strand is a braid.

28. The method of embodiment 27 wherein the distance between the third side and the opening is from about 65 to 75 percent of the exterior diameter of said butt adjacent to said distal end.

29. The method of embodiment 21 or 22 wherein the two ends of the suture strand are inserted into the blind hole.

30. The method of embodiment 29 wherein said suture strand is a monofilament.

31. The method of embodiment 30 wherein the distance between the third side and the opening is from about 65 to 70 percent of the exterior diameter of said butt adjacent to said distal end.

32. A machine having a first and a second die for crimping a surgical suture to a needle, the first die having a first and a second side that are essentially parallel, a third side that is curvilinear, and an opening, the opening being formed by the edges of the third side being in contact with the opposite edges of the first and second side; and the second die having a planar surface, the planar surface being essentially perpendicular to said first and second side and opposite to the third side of said first die, and the area of said planar surface being larger than the area of said opening of said first die.

DESCRIPTION OF THE INVENTION

It has been found that the attachment characteristics of a surgical suture to a surgical needle can be more precisely controlled by using this invention.

Besides the shape of the crimp and die more fully described herein, this invention uses a short crimp. A short crimp is one in which the crimped portion of the needle is less than the length of the suture end which is inserted into the needle. This provides an uncrimped section distally of the crimp. The uncrimped end of the suture must be pulled through the crimp to effect a pull-off.

By requiring that the uncrimped suture end be pulled through the crimp, as well as the friction of the suture in the crimp, it is practical to achieve consistent crimp retention, or a predetermined pull-out value.

In a manufacturing process, it is not practical to make separate measurements on each individual suture and needle before they are assembled, and then modify the degree of crimp for these particular measurements. Instead, it is necessary to use the same swage die settings. In practice, it is customary to use the same swaging die settings on a production run, with adjustments made if required by quality assurance.

From the production standpoint, it is feasible to test the maximum pull-out value on only representative samples, because the test is destructive and the samples are discarded after testing. Consequently, minimum pull-out values are usually the acceptable standard for quality assurance.

Figure 1:
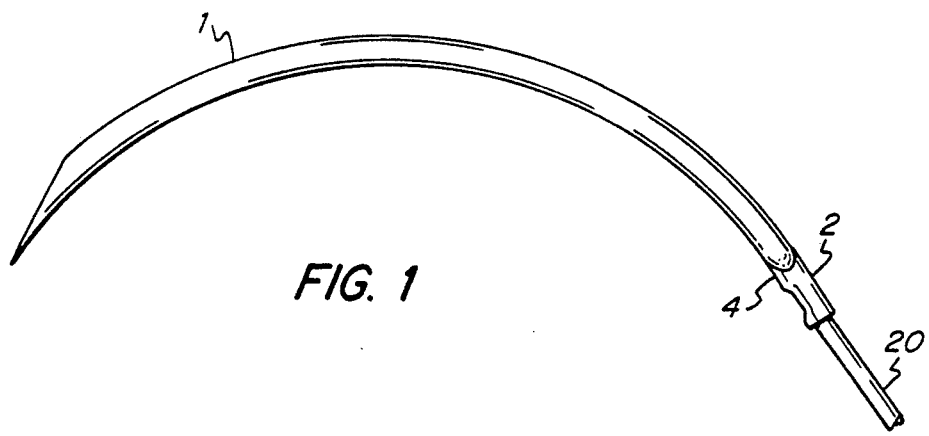
FIG. 1 is a partial side view of a needle-suture combination of this invention.
Figure 3:
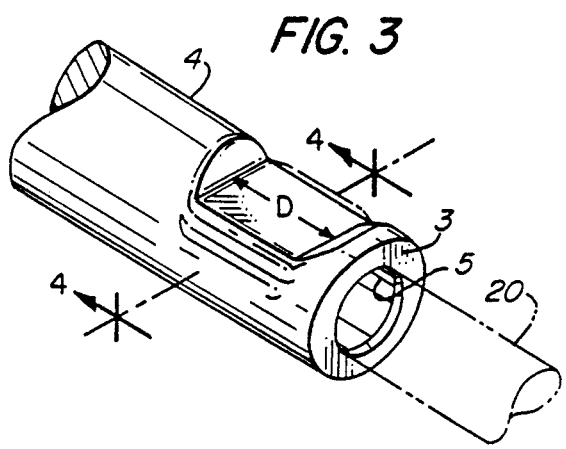
FIG. 3 is a partial perspective view of the needle-suture combination of FIG. 1 adjacent to the butt of the needle.
Figure 9:
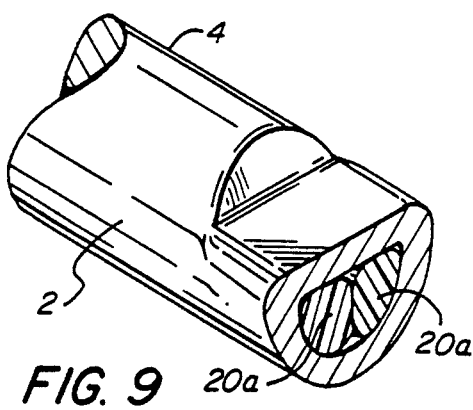
FIG. 9 is a sectional view of a alternative to the needle-suture combination of FIG. 7.

FIGS. 1 and 3 describe a needle-suture combination of this invention. FIGS. 7 to 9 describe an alternative needle-suture combination of this invention wherein both ends of the suture are inserted into the blind hole 5 of the butt 2 (fully shown in FIG. 6). The needle 1 comprises a butt 2. The butt has a proximal end 3 and a distal end 4. A blind hole 5 in the butt 2 originates at the proximal end 3. The termination point 5a of the hole 5 is at about the distal end 4 of the butt 2. A crimp, which is shown by the D dimension in FIGS. 3 and 7, and is intermediate the proximal end 3 and distal end 4 of the butt 2, attaches the needle 1 to the suture 20.

Referring to FIGS. 7 and 8, both ends of the suture 20 can be inserted into the butt 2 of the needle. The termination point 5a of the hole 5 (shown in FIG. 6) is at about the distal end 4 of the butt 2. The flat crimped portion 18 of the butt 2 is essentially synonomous with the D dimension, which for a looped monofilament suture is described in Table 3. For aesthetic and possibly other reasons, it is preferred to have an uncrimped portion 12 adjacent to the proximal end of the butt 2.

The conventional method for inserting both ends of the suture 20 into the blind hole 5 includes a plug 21. The plug 21 aids in maintaining both ends of the suture 20 in the blind hole 5 after crimping.

FIG. 9 is an alternative to the use of the plug 21 shown in FIGS. 7 and 8. Because of the geometrical design and dimensions of the crimp (shown, e.g., in FIGS. 5 and 6), and by controlling the diameter of the distal end 4 of the butt 2, it may be possible to eliminate the plug 21 while maintaining the integrity of both ends of the suture 20a in the blind hole 5.

Figure 2:
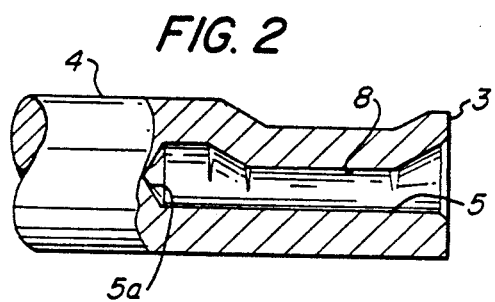
FIG. 2 is a partial, sectional side view showing a crimped blind hole in the butt of a needle.
Figure 4:
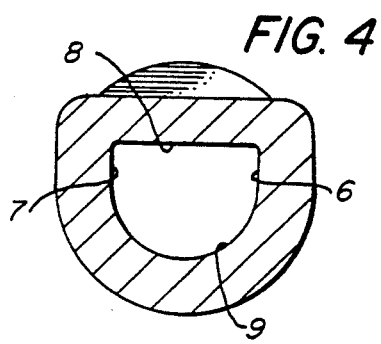
FIG. 4 is a front view of FIG. 2 taken along the plane 4—4 of FIG. 3.

Referring to FIGS. 2 and 4, the crimp comprises a first side 6 and a second side 7. The first side 6 and second side 7 are essentially parallel. A third side 8 is essentially perpendicular to the first and second sides. A fourth side 9 is curvilinear. The length of the curvilenear fourth side is at least about 1.1 times greater than the length of the third side. In one embodiment, the fourth side 9 is convex to the remaining first, second and third sides. The exterior distance between the third and fourth sides being, on the axial centerline, from about 65 to 85 percent of the exterior diameter of the butt 2 adjacent to the distal end 4. In a specific embodiment, the convex fourth side 9 is a semicircle.

Figure 5:
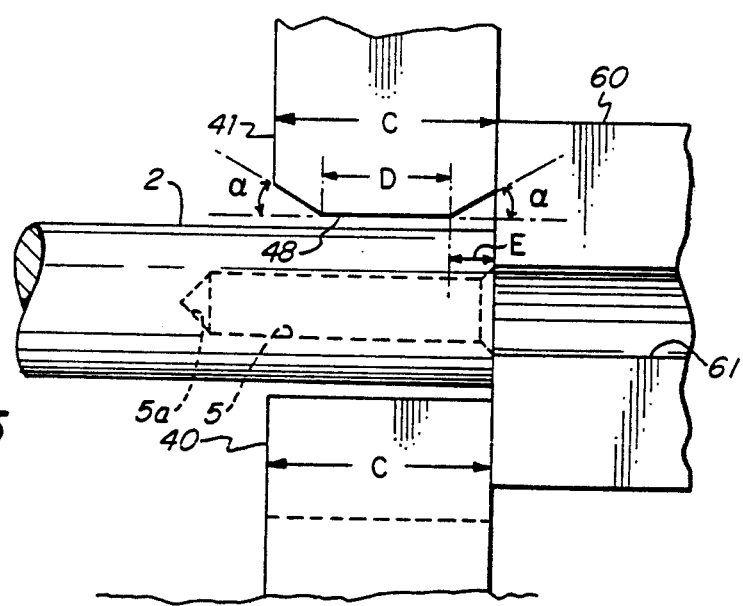
FIGS. 5 and 6 are side and front views, respectively, showing the relationship of the needle butt to the crimping dies, with FIG. 5 additionally showing the relationship of the blind hole to the threading block.
Figure 6:
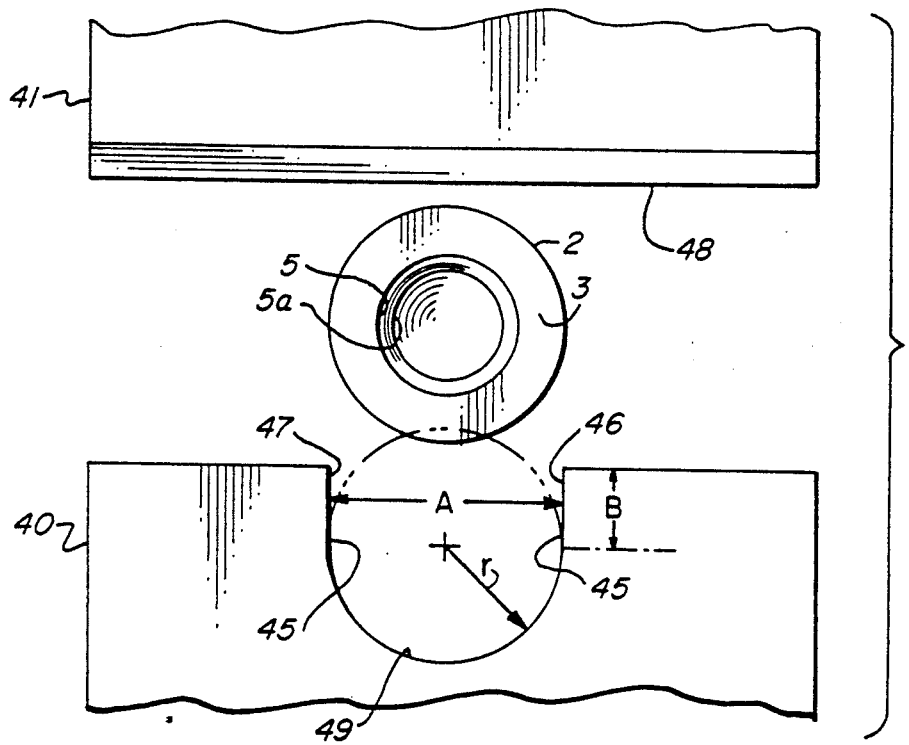
Figure 7:
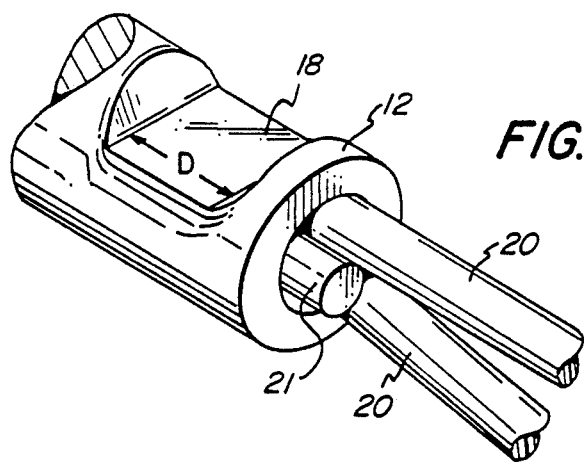
FIG. 7 is a partial perspective view of an alternative to the needle-suture combination of FIGS. 1 and 3.
Figure 8:
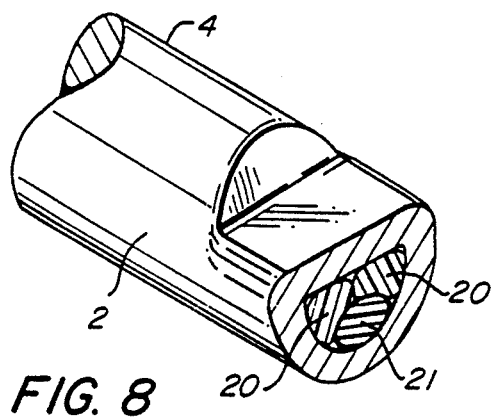
FIG. 8 is a sectional view of FIG. 7.

Referring to FIGS. 5 and 6, a machine for crimping the butt 2 of the needle shown in FIGS. 1 and 7 to 9 to the suture 20 is described. The machine comprises a first die 40 and a second die 41. The first die has a first side 46 and a second side 47. The first and second sides are essentially parallel. A third side 49 is curvilinear. In one embodiment, the curvilinear third side 49 is convex. In a specific embodiment, the convex third side is semicircular.

Referring again to FIGS. 5 and 6, an opening 45 is formed by the edges of the third side 49 being in contact with the opposite edges of the first 46 and second side 47. The second die 41 has a planar surface 48. The planar surface 48 is essentially perpendicular to the first side 46 and second side 47, and opposite to the third side 49 of the first die 40. The area of the planar surface 48 is larger than the area of the opening 45 of the first die 40.

The A, B+r, and C to E dimensions shown in FIGS. 5 and 6 (the D dimension is also shown in FIGS. 3 and 7) are more fully described in Tables 1 to 3. The r (radius) dimension shown in FIG. 6 and described in the tables is essentially identical to the outside radius of the butt 2.

TABLE 1[1]

| Uncrimped Needle Dia. (d)[2] | Single End Monofilament Suture | | | | |
|---|---|---|---|---|---|
| | Lower Die | | Both Dies | Upper Die | |
| | A[3] | (B + r)[4] | C | D | E |
| .050 | 0.0510 | 0.0400 | .065 | .045 | .010 |
| .044 | 0.0450 | 0.0350 | .065 | .045 | .010 |
| .039 | 0.0400 | 0.0300 | .065 | .045 | .010 |

TABLE 1-continued

| Uncrimped Needle Dia. (d)[2] | Single End Monofilament Suture | | | | |
|---|---|---|---|---|---|
| | Lower Die | | Both Dies | Upper Die | |
| | A[3] | (B + r)[4] | C | D | E |
| .034 | 0.0350 | 0.0270 | .065 | .045 | .010 |
| .032 | 0.0330 | 0.0260 | .065 | .030 | .010 |
| .028 | 0.0285 | 0.0220 | .065 | .030 | .010 |
| .026 | 0.0270 | 0.0200 | .065 | .030 | .004 |
| .024 | 0.0245 | 0.0170 | .045 | .020 | .004 |
| .022 | 0.0225 | 0.0160 | .045 | .020 | .004 |
| .020 | 0.0205 | 0.0142 | .035 | .020 | .002 |
| .017 | 0.0173 | 0.0121 | .035 | .015 | .002 |
| .015 | 0.0152 | 0.0107 | .035 | .015 | .002 |
| .013 | 0.0132 | 0.0092 | .035 | .015 | .002 |

[1]Tolerances for all die dimensions are +0.0005/−0.0000, except the E dimension which is +0.0010/−0.0000. All needle and die dimensions are in inches.
[2]The needle is manufactured from 420 Series stainless steel wire.
[3]Working and operable dimension = (1.02 ± .01)d; the dimensions shown are representative.
[4]Working dimension = (0.75 ± 0.05)d; operable dimension = (0.75 − 0.05/+0.10)d; the dimensions shown are representative.

TABLE 2[1]

| Uncrimped Needle Dia. (d)[2] | Single End Monofilament Suture | | | | |
|---|---|---|---|---|---|
| | Lower Die | | Both Dies | Upper Die | |
| | A[3] | (B + r)[4] | C | D | E |
| .33 | 0.0132 | 0.0092 | .035 | .015 | .002 |
| .38 | 0.0152 | 0.0107 | .035 | .015 | .002 |
| .43 | 0.0182 | 0.0130 | .035 | .020 | .002 |
| .53 | 0.0225 | 0.0160 | .045 | .030 | .002 |
| .58 | 0.0250 | 0.0170 | .045 | .030 | .002 |

[1]Tolerances for all die dimensions are +0.0005/−0.0000, except the E dimension which is +0.0010/−0.0000. All needle and die dimensions are in inches.
[2]The needle is manufactured from 300 Series stainless steel wire.
[3]Working and operable dimension = (1.02 ± .01)d; the dimensions shown are representative.
[4]Working dimension = (0.75 ± 0.05)d; operable dimension = (0.75 − 0.05/+0.10)d; the dimensions shown are representative.

TABLE 3[1]

| Uncrimped Needle Dia. (d) | Multiple End Monofilament Suture | | | | |
|---|---|---|---|---|---|
| | Lower Die | | Both Dies | Upper Die | |
| | A[3] | (B + r)[4] | C | D | E |
| .050[2a] | 0.0510 | 0.0325 | .065 | .045 | .010 |
| .062 | 0.0630 | 0.0405 | .065 | .045 | .010 |
| .118[2b] | 0.0470 | 0.0300 | .065 | .045 | .010 |
| .126 | 0.0510 | 0.0325 | .065 | .045 | .010 |
| .138 | 0.0550 | 0.0350 | .065 | .045 | .010 |
| .158 | 0.0630 | 0.0405 | .065 | .045 | .010 |

[1]Tolerances for all die dimensions are +0.0005/−0.0000, except the E dimension which is +0.0010/−0.0000. All needle and die dimensions are in inches.
[2a]The needle for sizes .050 and .062 is manufactured from 420 Series stainless steel wire. The dimensions are in inches.
[2b]The needle for sizes .118 to .158 is manufactured from 300 Series stainless steel wire. The dimensions are in millimeters.
[3]Working and operable dimension = (1.02 ± .01)d; the dimensions shown are representative.
[4]Working dimension = (0.65 ± 0.05/−0.0)d; operable dimension = (0.70 − 0.05/+0.10)d; the dimensions shown are representative.

Tables 1 and 2 describe the dimensions for crimping one end of a monofilament, surgical suture strand, which has been inserted into the blind hole 5 of the butt 2, e.g. as shown in FIGS. 1 and 3. The needles described in Tables 1 and 2 were manufactured from 420 and 300 series stainless steel, respectively.

Table 3 describes the dimensions for crimping both ends of a monofilament surgical suture strand, which has been inserted into the blind hole 5 of the butt 2, e.g. as shown in FIGS. 7 to 9. The needles described in this table were manufactured from 300 and 420 series stainless steel.

It is to be understood that the dimensions described in the Tables 1 to 3 can be adapted to other alloys, e.g. 455 series stainless steel. It is also to be understood that the dimensions shown in Table 3 are representative of dimensions which can be used for crimping one end of a braided surgical suture strand which has been inserted into the blind hole 5 of butt 2.

Referring further to FIGS. 5 and 6, a method of manufacturing a needle-suture combination has been invented. In the method, a threading block 60 is used. The threading block has a slot 61. The threading block 60 is moved adjacent to the proximal end 3 of the butt 2 such that the slot 61 is aligned with the blind hole 5 of the butt 2.

The α angle adjacent to the termination point 5a of the butt 2 shown in FIG. 5 may operably be from about 25° to 35°; for the discussions shown in Tables 1 to 3, the α angle was 30°. The α angle adjacent to the E dimension shown in FIG. 5 is not critical to the practice of the invention. However, at least for aesthetic and possibly for other reasons, it is preferred to offset the crimp from the proximal end 3 (shown in FIG. 6) of the butt 2. This α angle may operably be from about 25° to 45°; for the dimensions shown in Tables 1 to 3, this α angle was 30°.

I claim:

1. A surgical needle-suture combination comprising:
a needle having a butt, the butt comprising a proximal and a distal end, and having essentially a circular cross section adjacent to the distal end;
a blind hole in the butt, the hole originating at the proximal end and terminating at about the distal end of said butt;
a monofilament suture strand having two ends, the two ends of the strand inserted into the blind hole; and
a crimp adjacent to said butt, the improvement to the surgical needle-suture combination comprising the crimp having a first and a second side that are essentially parallel, a third side that is essentially perpendicular to the first and second side, and a fourth side that is curvilinear, the length of the curvilinear fourth side being at least about 1.1 times greater than the length of the third side, the exterior distance between the third and fourth sides on an axial centerline being from about 65 to 70 percent of the diameter of said butt adjacent to distal end.

2. The needle-suture combination of claim 1 wherein the fourth side is convex.

3. The needle-suture combination of claim 2 wherein the fourth side describes a semicircle.

4. A method of manufacturing a surgical needle-suture combination, the surgical needle having a butt, the butt comprising a proximal and a distal end, and having essentially a circular cross section adjacent to the distal end and a blind hole in the butt, the hole originating at the proximal end and terminating at about the distal end of said butt, and a monofilament suture having two ends and at least one filament, the method comprising:
placing said butt of said needle between a first and second die, the first die having a first and a second side that are essentially parallel, the exterior distance between the first and second sides being from about 1 ½ to 3 percent larger than the diameter of said butt adjacent to said distal end, a third side that is curvilinear, and an opening, the opening being formed by the edges of the third side being in contact with the opposite edges of the first and second side, the distance between the axial centerline of the third side and the opening formed by the first and second sides being from about 65 to 70 percent of the diameter of said butt adjacent to said distal end, and the second die having a planar surface, the planar surface being essentially perpendicular to said first and second side and opposite to the third side of said first die, and the area of said planar surface being larger than the area of said opening of said first die;

moving a threading block adjacent to said proximal end of said butt, the threading block having a slot;

aligning the slot of the threading block with said proximal end of said butt;

inserting the two ends of the suture into said threading block, through said slot and into the blind hole of said needle; and crimping said butt of said needle into the at least one end of said suture by closing said first and second die.

5. The method of claim 4 after the crimping step comprising individually testing the needle-suture combination to obtain a minimum pull-out value.

* * * * *